United States Patent [19]

Fischer et al.

[11] Patent Number: 5,139,509

[45] Date of Patent: Aug. 18, 1992

[54] PHACOEMULSIFICATION SYSTEM WITH HANDPIECE SIMULATOR

[75] Inventors: Michael J. Fischer, Jenkintown; Brian J. Kotowich, Langhorne, both of Pa.

[73] Assignee: Site Microsurgical Systems, Inc., Horsham, Pa.

[21] Appl. No.: 398,581

[22] Filed: Aug. 25, 1989

[51] Int. Cl.$^5$ ............................................. A61H 1/00
[52] U.S. Cl. ............................... 606/107; 606/169; 606/170; 606/171; 604/22; 128/24 AA
[58] Field of Search ............ 128/24 A, 661.06, 423 R; 604/22; 606/37, 38, 45, 169, 172, 173, 107, 170, 171; 310/313 R, 313 A, 316, 317; 433/86; 73/661, 1 DV; 324/511, 83 FE

[56] References Cited

U.S. PATENT DOCUMENTS

| | | | |
|---|---|---|---|
| 2,932,189 | 4/1960 | Carlin | 73/570 |
| 3,223,194 | 12/1965 | Michael | 73/570 |
| 3,391,571 | 7/1968 | Johanson | 310/368 |
| 4,492,107 | 1/1985 | Sandhu | 73/570 |
| 4,587,958 | 5/1986 | Noguchi et al. | 128/24 AA |
| 4,658,819 | 4/1987 | Harris et al. | 606/38 |
| 4,689,993 | 9/1987 | Slettemoen | 73/579 |
| 4,716,897 | 1/1988 | Noguchi et al. | 606/37 |
| 4,768,496 | 9/1988 | Kreizman et al. | |
| 4,827,911 | 5/1989 | Broadwin et al. | 128/24 AA |
| 4,862,889 | 9/1989 | Feucht | 606/38 |

Primary Examiner—David M. Shay
Attorney, Agent, or Firm—Joel R. Petrow

[57] ABSTRACT

A phacoemulsification system is provided, including an ultrasonic phacoemulsification handpiece and a handpiece driver. A handpiece simulator is provided to analyze the performance characteristics of the handpiece driver. The simulator is selectively coupled in a feedback loop with the driver so as to receive drive signals from the driver and return a feedback signal to the driver in the same manner as a handpiece. The simulator detects the frequency and voltage characteristics of the signal provided by the handpiece driver and on the basis thereof generates a feedback signal for return to the handpiece driver. The simulator can exercise the response of the driver dynamically by controllably varying the frequency of the feedback signal. The simulator may be constructed in either analog or microprocessor-based form. In the latter case, the microprocessor can determine whether the drive signals are within acceptable limits, and displays to the user the nature of unacceptable performance.

6 Claims, 4 Drawing Sheets

PHACOEMULSIFICATION SYSTEM WITH HANDPIECE SIMULATOR

This invention relates to systems for performing surgery through the ultrasonic emulsification of tissue and, in particular, to circuit which electronically simulates a handpiece which ultrasonically emulsifies tissue.

Phacoemulsification handpieces are commonly used in surgery for the removal of tissue and other bodily materials. In opthalmic surgery such handpieces are widely used to remove cataracts from the eye. The handpiece is energized by a piezoelectric stack which vibrates the workpiece connected at the end of the handpiece. The piezoelectric stack will ultrasonically vibrate the workpiece in small amplitude oscillations at a frequency of many thousand kilohertz. When the vibrating tip of the workpiece contacts a cataract, the cataract tissue is chopped into fine pieces, which can be flushed and removed through irrigation of the surgical site and aspiration of the emulsified material. Such removal of cataracts through phacoemulsification is efficient, precise, and enables removal of the cataract without significant damage to surrounding eye tissue.

A phacoemulsification handpiece is conventionally powered by a handpiece drive instrument. The handpiece is detachable from the instrument so that it can be sterilized, and to enable the use of different types of handpieces and workpieces with the same drive instrument. Typically the drive instrument provides a controllable energizing signal to the piezoelectric stack which vibrates the workpiece. The drive instrument also receives a feedback signal from a second piezoelectric stack to the rear of the drive stack. The feedback signal is sensed as a measure of the operation of the handpiece and the drive signal adjusted in response to variances of the feedback signal. This completes a feedback loop of the two piezoelectric stacks and the circuitry in the drive instrument, enabling the circuitry to continually monitor and adjust the performance of the handpiece during surgery.

However, in such a feedback loop diagnosis of a failure is difficult when an element of the feedback loop fails or suffers from deteriorating performance. Once an element in the loop fails, the performance of the entire loop is affected. All that the surgeon knows is that his surgical system is inoperative or ineffective. It would be desirable in such a situation to enable the surgeon to be able to diagnose the system failure, and at least be able to determine whether the failure is in the handpiece or the drive circuitry. If the surgeon was able to determine that the drive circuitry was not the source of the problem, for instance, the surgeon could detach the defective handpiece and replace it with a new one, knowing that the drive circuitry was operating properly and that surgery could proceed with the use of the new handpiece.

In accordance with the principles of the present invention, a handpiece simulator is provided which enables diagnosis of the drive circuitry of a phacoemulsification handpiece. The simulator is preferably incorporated in the same instrument as the drive circuitry, where it is available to diagnose the handpiece drive circuitry any time a system failure occurs or is suspected. When such a failure occurs, the drive signal output and the feedback signal input of the drive circuitry are connected to the simulator. The simulator receives the drive signal and in response thereto generates a feedback signal in the same manner as a phacoemulsification handpiece. The simulator in this environment also develops an output signal to inform the user as to the quality of operation of the handpiece drive circuitry. The output signal will tell the user if the drive circuitry is defective and in need of repair, or whether the drive circuitry is operating properly, in which case the handpiece is the source of the problem. In a preferred embodiment the handpiece simulator would automatically perform a check of the drive circuitry each time the instrument is initially energized, and would also be activatable under user control if a failure occurs during use of the instrument. The simulator would also be useful in a stand-alone environment by service personnel when diagnosing failures in phacoemulsification handpiece systems.

Figure 1:
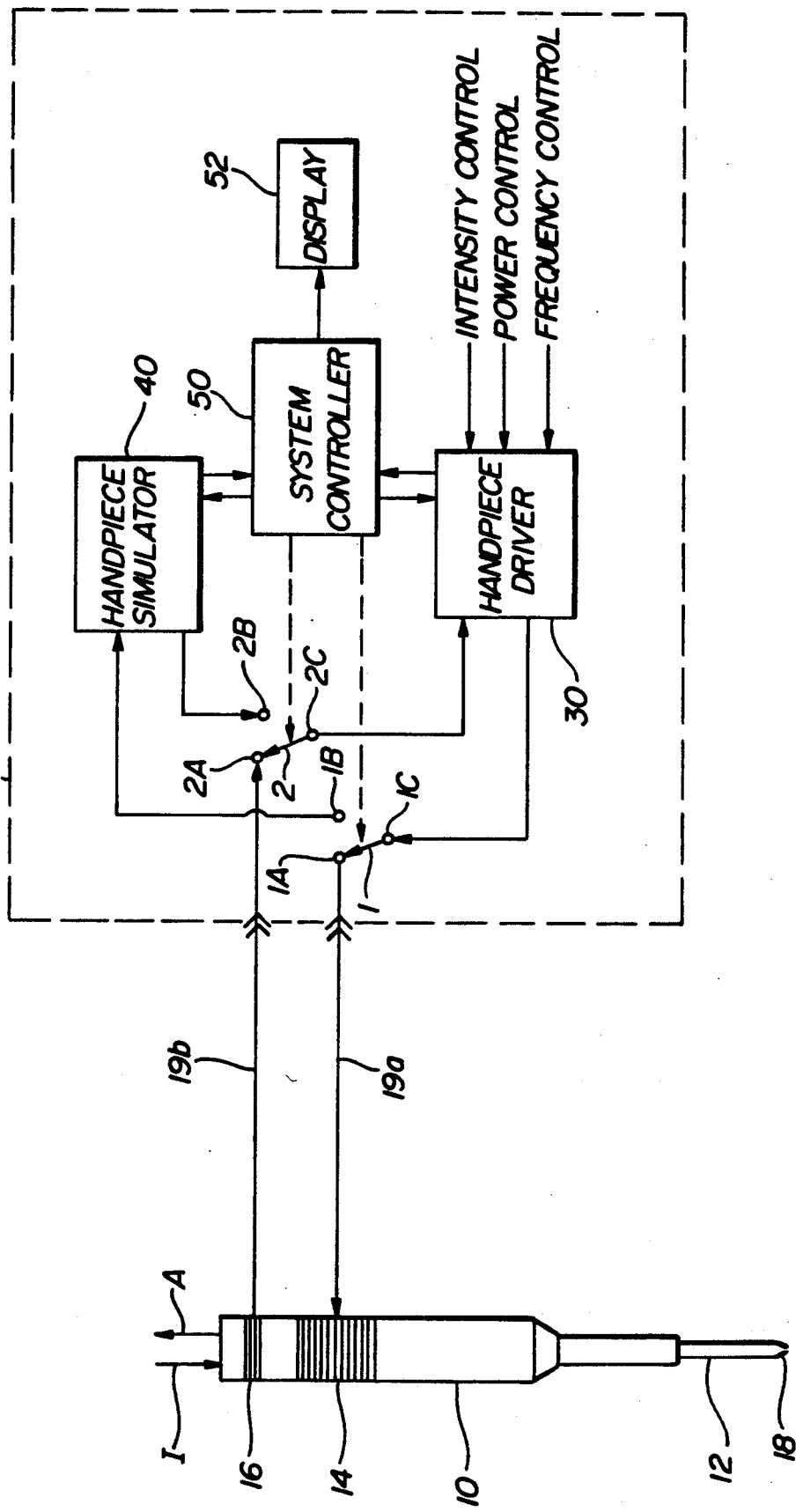
FIG. 1 is a block diagram of a phacoemulsification handpiece system constructed in accordance with the principles of the present invention.

Referring first to FIG. 1, a phacoemulsification handpiece system constructed in accordance with the principles of the present invention is shown. A handpiece 10 is shown, which generally resembles a thick pencil. A detachable workpiece 12 is mounted at the distal end of the handpiece. The workpiece 12 is vibrated at ultrasonic frequencies by a piezoelectric drive stack 14 located in the handle portion of the handpiece. In the illustration of FIG. 1 the workpiece 12 is hollow with a tapered tip 18. In use, the surgical site is infused with a flow of solution, and tissue which is emulsified by the vibrating tip is aspirated through the hollow workpiece. The arrows I and A at the proximal end of the handpiece schematically represent the connection of irrigation and aspiration lines to the handpiece.

The ultrasonic vibrations of the piezoelectric stack 14 are transmitted to the workpiece 12 through intervening connecting elements of the handpiece. Conventionally the ultrasonic waves have a nodal point which forms the connection between the inner, vibrating members of the handpiece and the handpiece case which is held by the user. By connecting the case at the nodal point, the vibrations transmitted to the user's hand are greatly diminished.

Located proximal the stack 14 is a second piezoelectric stack 16, which also receives ultrasonic vibrations generated by the drive stack 14. In response to the receipt of these vibrations the second stack 16 generates an electrical signal which is fed back to the circuitry of the handpiece drive module 20. The signal produced by the stack 16 is thus a measure of the performance of the drive stack and the handpiece, and is used by the circuitry in the module 20 as a feedback signal to constantly adjust and control the drive signal applied to the drive stack 14.

The module 20 includes handpiece driver circuitry 30 which responds to the settings of controls, such as the illustrated intensity control, power control, and frequency control, and the feedback signal generated by the second stack 16 to develop a drive signal for the drive stack 14 of the handpiece. In the embodiment of FIG. 1 the handpiece driver 30 is connected to the drive stack 14 of the handpiece by a cable 19a, and the feedback signal is returned to the driver 30 by a cable 19b. These cables are detachable to enable the connection of various handpieces to the drive module. The drive and feedback signals are connected to cables 19a, 19b through the terminals 1A, 1C and 2A, 2C of two switches 1 and 2 when the arms of the switches are set as shown in FIG. 1. The handpiece driver circuitry is conventional, and may be of the type presently available in the Site TXR ™ Phaco module available from Site Microsurgical Systems of Horsham, Pa.

In accordance with the principles of the present invention the module 20 also includes a handpiece simulator 40. The handpiece simulator 40 is capable of receiving the handpiece drive signal from the driver 30 and, in response thereto, producing a commeasurate feedback signal. The handpiece simulator 40 may be switched by resetting switches 1 and 2 to their alternate positions to connect the simulator to the driver. Under control of a system controller 50, which in the preferred embodiment would include a microprocessor, switches 1 and 2 are reset to connect the simulator to the driver when the module is initially energized, or under manual control by the user whenever the user suspects a system malfunction. By measuring signal levels at various test points of the simulator, as discussed below, the controller determines whether the performance of the handpiece driver is within proper limits, and displays the results of this determination on a display 52.

Figure 2:
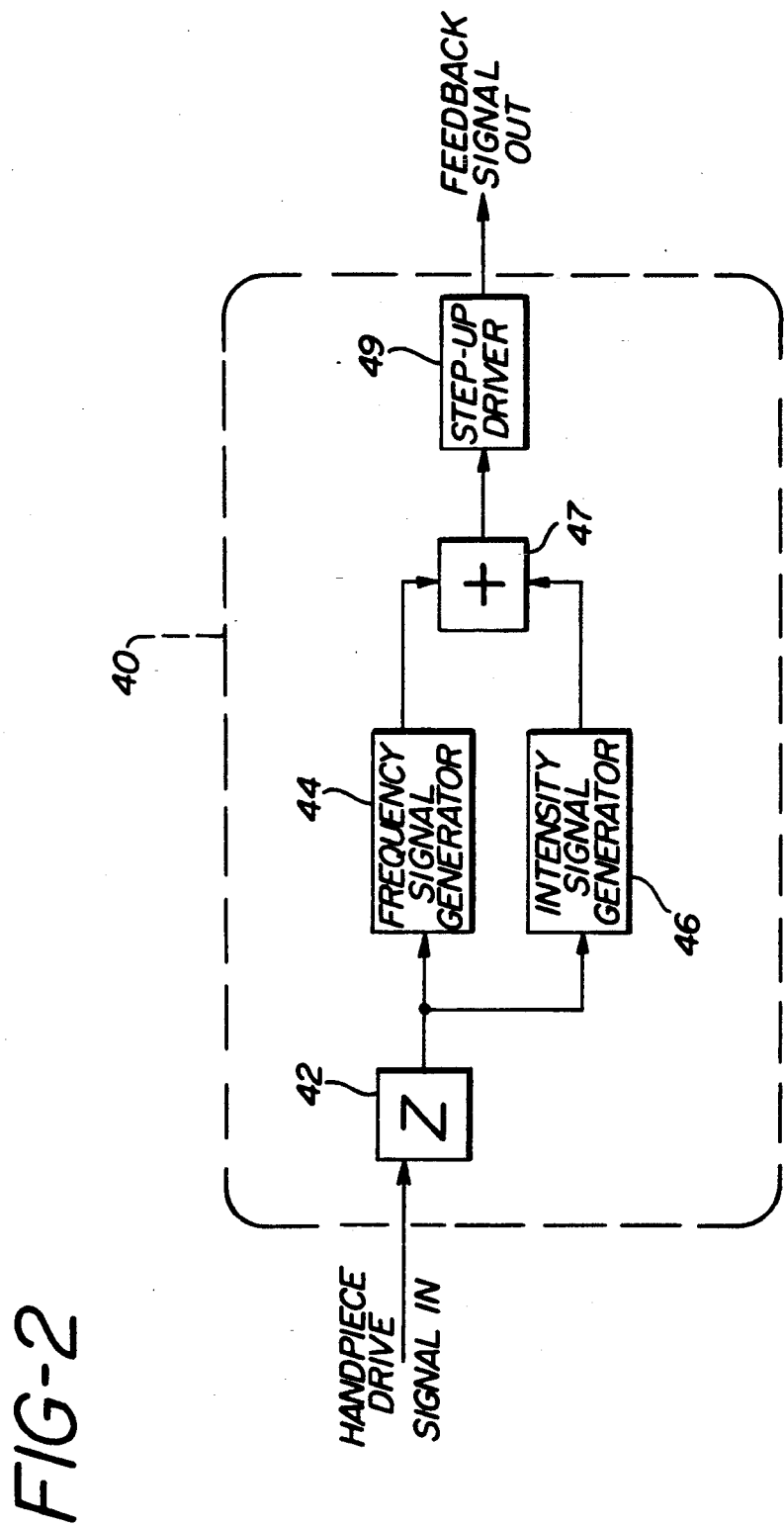
FIG. 2 is a block diagram of the phacoemulsification handpiece simulator of the system of FIG. 1.

FIG. 2 is a more detailed block diagram of the handpiece simulator 40 of FIG. 1. At its input the simulator receives the handpiece drive signal from the driver 30. This signal is applied to an impedance element 42, at which measurements can be taken of the power delivered by the driver. Following the impedance element 42 the drive signal is processed by two parallel paths, one including a frequency signal generator 44 and the other including an intensity signal generator 46. The frequency signal generator 44 develops an output signal having a frequency appropriate to a feedback signal that is responsive to the drive signal. The intensity signal generator develops an output signal having an intensity appropriate to a feedback signal that is responsive to the drive signal. Frequency and intensity parameters may be measured at any point in the simulator following these generators. The frequency and intensity representative signal are combined by a combiner 47 to produce a signal having a frequency and an intensity appropriate to a responsive feedback signal. This low level signal is stepped up in voltage by a step-up driver 49 to produce the simulated handpiece feedback signal, which is returned to the feedback signal input of the handpiece driver.

Figure 3:
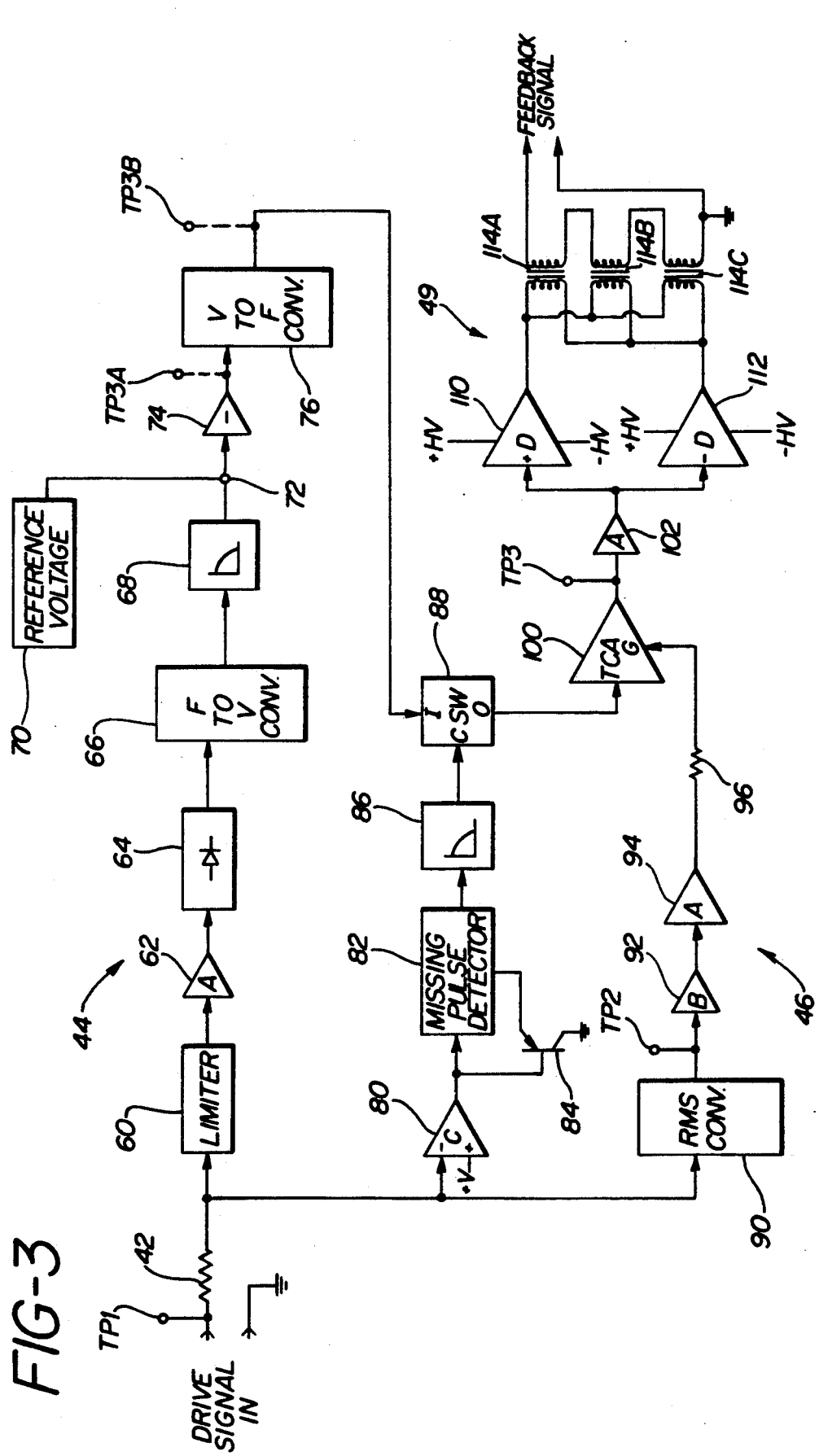
FIG. 3 is a detailed description in schematic and block diagram form of the handpiece simulator of FIG. 2.

FIG. 3 is a schematic and block diagram of the handpiece simulator of FIG. 2. In the following discussion of this FIGURE, the parenthetical notations are to commercially available integrated circuit device types that may be employed in the construction of the simulator. The drive signal from the handpiece driver is applied to a resistive impedance 42. At test point TP1 is located at the input side of the impedance 42. The frequency signal generator 44 is comprised of two parallel paths, the upper one including a diode limiter 60 which clips and squares the input signal. The limited signal is amplified by a gain stage 62 (OP27) and the negative-going portion of the signal is clipped by a diode 64. The resultant unipolar signal is now in a digital form, and is applied to a frequency to voltage converter 66 (LM2907) which produces a voltage proportionate to the input signal frequency. This voltage is filtered by a low pass filter 68 (324) and applied to a node 72. Also applied to the node 72 is a pedestal voltage from a reference voltage source 70 (1403; 324). The pedestal voltage applied to the node insures that a positive potential will be present initially at the node. This will provide system stability in the event that the handpiece simulator is actuated upon power-up of the module, during which time the feedback loop may still be in the process of stabilizing. The voltage at the node, which is a combination of that Produced by the converter 66 and the reference voltage generator, is coupled by an inverter 74 (324) to a voltage to frequency converter 76 (2206). The converter 76 will produce an output signal with a frequency that is a function of the voltage applied at its input. In a constructed embodiment the pedestal voltage was calibrated to produce a 60 KHz signal at the output of the converter 76, and as the voltage derived from the drive signal began to contribute to the net voltage at the node 72, driving the net voltage higher, the increasing voltage at the input of the converter 76 acted to decrease the frequency of the output signal of the converter as the feedback loop began to stabilize. In a preferred embodiment the reference voltage source is operated under control of the system controller to apply various pedestal voltages to the converter 76 depending upon the frequency of the handpiece being simulated, or is stepped over a range of pedestal voltages to exercise and test the response of the handpiece driver to different handpiece modes of operation. FIG. 3 also shows the possible connection of two test points, TP3A and TP3B, at the input and output of the converter 76. The use of these test points will be discussed below.

The frequency signal produced by the converter 76 is applied to the input of a solid state switch 88 (DG201). The frequency signal will be coupled to the output of the switch 88 depending upon the state of the signal at the control input of the switch. The control signal for the switch begins with the drive signal at the impedance 42, which is applied to a comparator 80 (339). The output of the comparator 80 is coupled to a missing pulse detector 82 (555) which operates with feedback provided by a transistor 84. The missing pulse detector develops a bistate output signal depending upon the continuous nature of the drive signal. If the drive signal is continuous, the detector 82 produces a signal of one state; if the drive signal is discontinuous, a signal of the other state is produced. The detector output signal is filtered by a lowpass filter 86 (339) and is coupled to the control input of the switch 88. Thus, if the drive signal is continuous the frequency signal is passed by the switch; if the drive signal is discontinuous, the frequency signal is not passed. The output of the switch 88 is coupled to the input of a transconductance amplifier 100 (CA3080).

The intensity signal generator is shown in the bottom path in the drawing and has as its input signal the drive signal of the impedance element 42. The drive signal is applied to the input of an RMS converter 90 (AD536), which has a test point TP2 at its output. The RMS converter provides a full wave rectification of the input signal and produces a DC output signal. This DC signal is buffered by a buffer 92 (CA3146) and is amplified by an amplifier 94 (OP27). The amplified signal is dropped across a resistor 96 to develop a current, which is applied to the gain control input of the transconductance amplifier. Thus, the transconductance amplifier receives the frequency signal at its input and amplifies this signal as a function of the intensity signal applied to its gain control input. The output signal of the transconductance amplifier 100 thus has the frequency and intensity characteristics of a feedback signal appropriate to the drive signal from the handpiece driver. This signal may be measured at test point TP3 at the output of the transconductance amplifier 100.

The output signal of the transconductance amplifier 100 is buffered by a buffer 102 (3140) and stepped up in voltage by the step-up driver 49. The buffered signal is applied to the inputs of complementary high current amplifiers 110 and 112. The outputs of amplifiers 110 and 112 are coupled to the primary windings of three transformers 114A, 114B, and 114C, which are connected in parallel. The secondary windings of the transformers are coupled in series to provide the high voltage feedback signal which is returned to the handpiece driver.

In operation the handpiece driver may be set to drive a handpiece at a given intensity and power level, and at a given frequency, for instance in the range of 54-56 KHz. When the handpiece simulator is initially connected to the handpiece driver the start-up drive signal may be in the range of 40-50 KHz, for example. The feedback signal from the simulator will thus have a frequency primarily determined by the pedestal voltage, around 60 KHz, and will be of a low intensity and power. But as the feedback loop of the simulator and driver begins to stabilize, the intensity will increase, thereby increasing the gain of the transconductance amplifier, and the frequency will decrease toward the desired range. When the loop has stabilized, measurements can be taken to ascertain the performance of the loop and the handpiece driver. For instance, the input signal provided by the handpiece driver is present at TP1 and the voltage level on the other side of the impedance 42 is present at TP2. By converting the signal at TP1 to a DC voltage with an RMS converter similar to converter 90 and comparing the converter signal with that present at TP2, the power delivered by the handpiece driver may be ascertained. The signals present at TP3 and TP3A provide information as to the frequency characteristics of the signal provided by the driver. The signal at TP3 represents the characteristics of the feedback signal and also the intensity of the driver signal by reason of the intensity control signal supplied to the gain control input of the transconductance amplifier. Hence the measurement and use of the signals at the indicated test points may be used to determine the critical characteristics of the signals provided by the handpiece driver 30.

Figure 4:
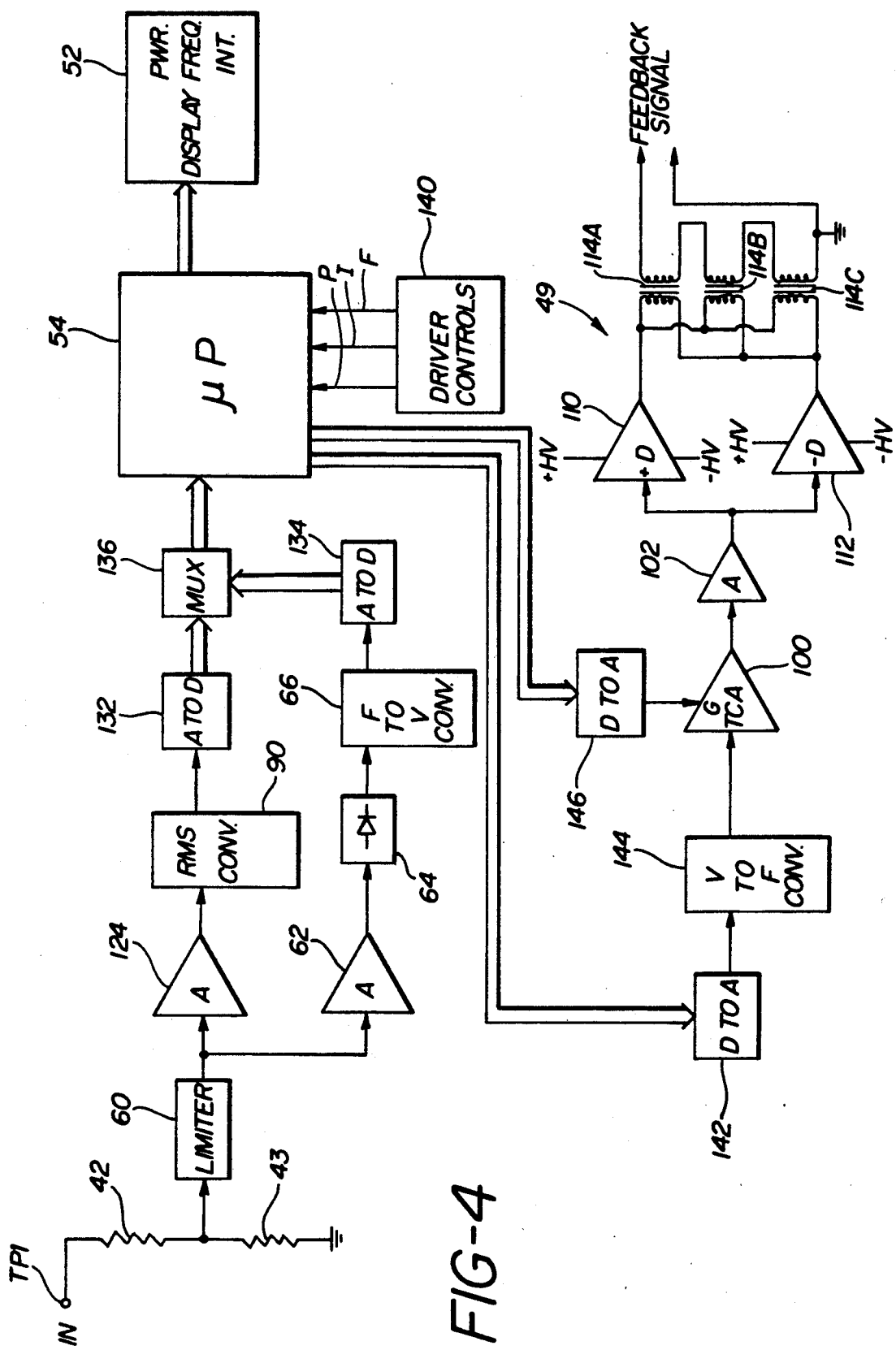
FIG. 4 illustrates an embodiment of the present invention utilizing a microprocessor-based controller.

FIG. 4 illustrates an embodiment of a handpiece simulator of the present invention in which the system controller 50 includes a microprocessor 54. The simulator input signal from the handpiece driver 30 is applied to the input terminal TP1. The input signal which is nominally a 210 volts rms signal at approximately 55 KHz is dropped across resistors 42 and 43. A signal at approximately 6-8 volts rms is tapped off at the junction to the two resistors and applied to the input of a limiter 60 as in the embodiment of FIG. 3. The limited signal is buffered by an amplifier 124 and applied to the input of an RMS converter 90 which produces a DC signal that is a measure of the voltage of the input signal to the simulator. The DC voltage produced by the RMS converter 90 is digitized by a 12 bit analog to digital (A to D) converter 132 and the digital signal samples are applied to one input of a multiplexer 136.

In a parallel path the signal produced by the limiter 60 is buffered by an amplifier 62 and converted to a unipolar signal by a diode 64. The unipolar signal is applied to a frequency to voltage converter 66 which produces a DC voltage in the range of 0-10 volts in correspondence to a signal frequency range of 40-60 KHz. The DC voltage produced by the converter 66 is sampled by a 16 bit A to D converter 134 and the digital samples are applied to a second input of the multiplexer 136. Under control of the microprocessor 54 the multiplexer alternately steers digital samples from the two A to D converters to the microprocessor for storage and analysis.

Signals representative of the power, intensity and frequency characteristics desired of the handpiece drive signal are provided by driver controls 140. These signals are used to control the handpiece driver 30, and are also provided to the microprocessor 54 to inform the microprocessor of the demand placed to the handpiece driver. On the basis of the required signal characteristics the microprocessor can analyze the measured voltage and frequency signal samples to ascertain whether the handpiece driver is operating properly. This may be done by calculating algorithms using the information received by the microprocessor, or may be done by comparing the signal samples over time with table look-up values to see that the sampled signal characteristics are within acceptable limits. If the received signals are found to be outside the ranges of acceptable levels the microprocessor will send an appropriate signal to a display 52 to inform the user of the signal characteristic found to be deficient.

The microprocessor 54 will also use the information it receives to produce necessary signal components for the generation of a feedback signal to be returned to the handpiece driver. A 16 bit digital signal representative of the frequency of the feedback signal is applied to the input of a digital to analog (D to A) converter 142. The output of the D to A converter 142, typically in the range of 0 to 10 volts, is applied to a voltage to frequency converter 144 which generates an a.c. signal in a typical frequency range of 40-60 KHz. The output signal of the converter 144 is applied to the input of transconductance amplifier 100. An 8 bit digital signal representative of the gain control signal for the transconductance amplifier is applied by the microprocessor to the input of a D to A converter 146. The gain control output voltage produced by the D to A converter 146 has a typical dynamic range of 20 volts and is applied to the gain control input of the transconductance amplifier 100. The illustrated components following the transconductance amplifier and used to produce the feedback signal for the handpiece driver function in the same manner as in the embodiment of FIG. 3.

As mentioned above, the results of the analysis and comparisons made by the microprocessor 54 are displayed to the user on a display 52 under control of the microprocessor. The display could simply illuminate selectively a red or a green light or LED for each function, thereby informing the user not only whether the handpiece driver is functioning properly, but the signal characteristic(s) which is the source of a problem. The latter information is of considerable assistance to a repairman who is repairing a system which has failed in a particular respect. In a preferred embodiment the display would be an alphanumeric liquid crystal display which displays not only system performance as being within or outside the predetermined system limits, but also a quantified representation of system performance. As an example, such a display would show the exact frequency at which the driver-simulator loop stabilized. The microprocessor 54 could also be used in conjunction with the analog embodiment of FIG. 3 to produce output signals for control of reference voltage generator 70 to step the pedestal voltage over a range of frequency-representative voltages. In the embodiment of FIG. 4 such stepping of the frequency would be accomplished by stepping the digital values applied to the D to A converter 142. In either case, such frequency stepping would exercise the handpiece driver so as to determine the driver's response to a sequence of simulated frequency value offsets of a phacoemulsification handpiece, such as those that may occur during use of a handpiece in opthalmic surgery.

What is claimed is:

1. A handpiece driver system for emulsifying tissue during surgery comprising:
    a handpiece driver having an electrical output, the output of said driver producing an electrical drive signal controlled by a control means and electrically connected to a handpiece,
    a feedback loop electrically connecting said handpiece, driver and control means;
    a handpiece simulator;
    means for selectively, electrically switching said handpiece or said handpiece simulator into said feedback loop with said handpiece driver and control means; and
    said handpiece simulator including means for electrically replacing said handpiece in said feedback loop containing said handpiece driver and said control means, said handpiece simulator including means for receiving a drive signal from said handpiece driver and containing a frequency generator means for producing a frequency appropriate to a feedback signal responsive to the drive signal and an intensity signal generator means for producing an intensity appropriate to a feedback signal also responsive to said drive signal, said handpiece simulator further comprising a means for electrically combining said frequency and intensity signals to generate an electrical feedback signal to said handpiece driver in electrical connection therewith, and said handpiece simulator including means for providing an indication to a user of the performance of said handpiece driver.

2. The system of claim 1, wherein said handpiece simulator further includes means, responsive to said drive signal, for inhibiting said feedback signal in the presence of a discontinuous drive signal.

3. The system of claim 1, wherein said handpiece simulator further includes means for offsetting the frequency of said feedback signal as a function of said drive signal.

4. The system of claim 1, further including driver controls and a display, coupled to said handpiece driver and said control means, said driver controls including means for controlling said handpiece driver and said display including means for displaying signal characteristics provided to said control means.

5. The system of claim 1, wherein said control means includes a microprocessor, responsive to electrical characteristics of said drive signal, for providing said feedback signal.

6. The system of claim 5, wherein said control means controls said display means to provide indications of the power, frequency, and intensity characteristics of said drive signal.

* * * * *